United States Patent [19]

Ciosek, Jr.

[11] 4,369,653
[45] Jan. 25, 1983

[54] SHRINKAGE GAUGE AND METHOD

[75] Inventor: Bernard M. Ciosek, Jr., Wilmington, Del.

[73] Assignee: E. I. Du Pont de Nemours and Company, Wilmington, Del.

[21] Appl. No.: 251,990

[22] Filed: Apr. 6, 1981

[51] Int. Cl.³ .................... G01N 33/38; G01N 33/34
[52] U.S. Cl. .................... 73/150 R; 73/432 R; 33/147 N
[58] Field of Search .................... 73/16, 432 R, 432 G, 73/150 R; 33/143 M, 143 J, 143 L, 143 T, 147 N

[56] References Cited

U.S. PATENT DOCUMENTS

| | | | |
|---|---|---|---|
| 2,428,234 | 9/1947 | Mapp | 171/242 |
| 2,500,836 | 3/1950 | Lathrop | 33/143 L |
| 2,656,712 | 10/1953 | Comstock | 73/16 |
| 3,779,085 | 12/1973 | Rice | 73/432 R |
| 3,937,212 | 2/1976 | Fletcher et al. | 128/25 |
| 4,054,049 | 10/1977 | Egger | 73/16 |
| 4,204,544 | 5/1980 | Feldstein et al. | 128/242 |
| 4,211,013 | 7/1980 | Bresson et al. | 33/147 R |
| 4,229,883 | 10/1980 | Kobashi | 33/143 L |

Primary Examiner—S. Clement Swisher

[57] ABSTRACT

A gauge and method for measuring the cure shrinkage of polymeric concrete. Blades dependent from a bridge are inserted in poured concrete. Movement of the blades with the concrete is measured by a proximity sensor and associated instrumentation records the movement continuously during the cure cycle.

9 Claims, 5 Drawing Figures

SHRINKAGE GAUGE AND METHOD

BACKGROUND

This invention relates, generally, to the use of cementitious materials and, more particularly, to tests and measurements of such materials as they cure.

Available techniques for measuring the cure shrinkage of fast setting, polymeric concrete and other cementitious materials involve usage of long calipers or internal strain gauges. Comparisons of results obtained with calipers have shown inaccuracies, a lack of precision and inconsistencies between operators. Data obtained with strain gauges show comparatively low shrinkage values, probably due to friction and/or stiffness of the gauge. The data also show variations in shrinkage with unavoidable variations in alignment of the gauge.

Where used herein, the term "cementitious materials" is meant to include mortars, filled mortars and concrete, with either portland cement, a resin system or one of the commercially available, monomeric systems as the bonding agent. Typical examples of the latter are the CRYLCON ® methacrylate bonding agents produced by the assignee hereof.

SUMMARY

Consistent and accurate measurements of shrinkage during curing of cementitious materials have been obtained with the gauge of the present invention. The shrinkage gauge has a pair of parallel blades dependent from a bridge member. One blade is fixed, the other slidable, with respect to the bridge. A releasable pin locks the slidable blade with respect to the bridge member until the gauge has been inserted in poured, cementitious materials. A proximity transducer that is fixed to the bridge has a probe spaced from and aligned with a target that is fixed with respect to the slidable blade.

According to the method of the invention, a mold box is lined with a plastic film and cementitious materials are poured into the lined box. Then, the blades of the gauge are sunk in the poured materials and the locking pin is released. As the materials cure, relative movement of the blades is measured and recorded continuously as an indication of unrestrained expansion and/or shrinkage.

DRAWINGS

FIG. 5 is a side elevation of a modification.

DETAILED DESCRIPTION

Figure 1:
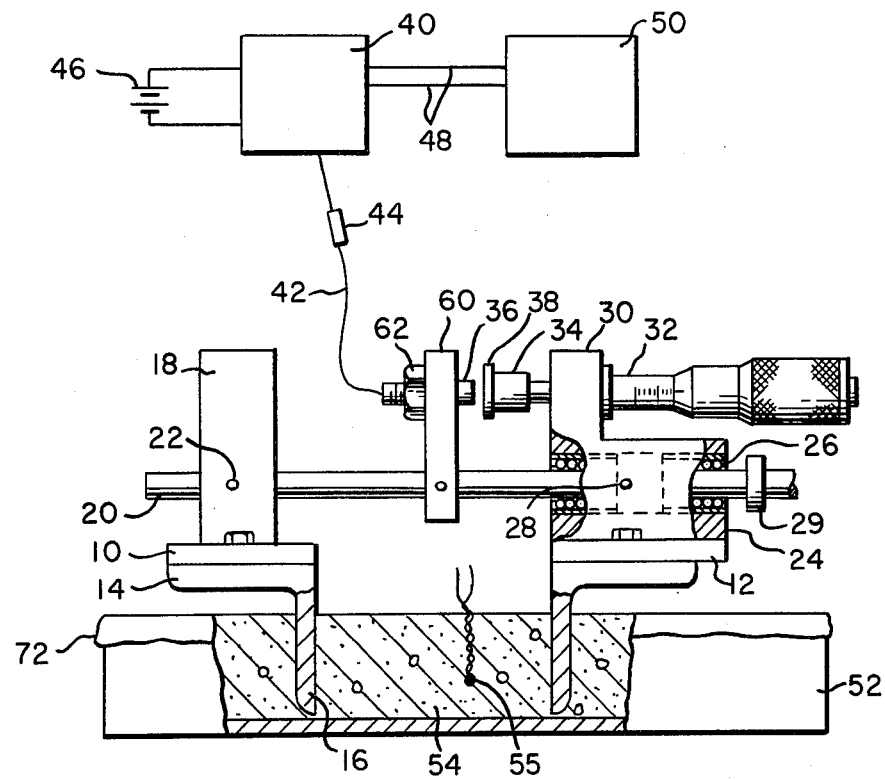
FIG. 1 is a side elevation of the shrinkage gauge of the present invention and includes a block diagram of associated components.
Figure 2:
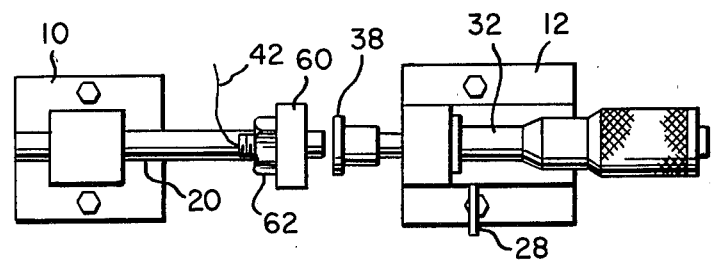
FIG. 2 is a top view of the gauge.
Figure 3:
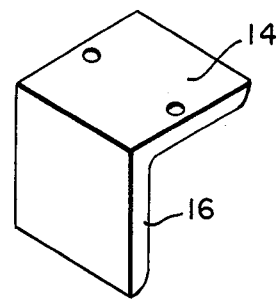
FIG. 3 is an enlarged, perspective view of one of the blades shown in FIG. 1.

Referring now to FIGS. 1-3, the shrinkage gauge has two blade feet, one attached to a base plate 10, the other to a base plate 12. Each foot has an apertured mounting plate 14 and a wide, dependent blade 16. The blades are in substantial parallelism. Base plate 10 is fastened to the bottom of an end block 18 that is bored to receive a bridge member in the form of a shaft 20. Block 18 is fixed with respect to shaft 20 by a set screw 22. Base plate 12 is fastened to the bottom of a slide block 24. A bore through block 24 is provided with ball bushings 26 that receive shaft 20. Blades 16 can be fixed a set distance apart by a locking pin 28 that extends through a hole in block 24 into an aperture in shaft 20. Sliding movement of block 24 away from block 18, with pin 28 removed, is limited by a stop member 29 on shaft 20. An upright projection 30 on block 24 is bored and split to receive a micrometer head 32 with an attached target 34 for a proximity transducer 36. Target 34 includes a metallic sleeve that fits on the end of micrometer 32 by friction and an integral disc 38 that is conductive.

The proximity transducer 36 is connected to a proximeter 40 by a cable 42, which includes a connector 44. The proximeter is also connected to a direct current (DC) power supply 46. The output from proximeter 40 is transmitted by leads 48 to a strip chart recorder 50. The shrinkage gauge, as shown in FIG. 1, is placed in a mold box 52 so that the blades 16 rest on or near the bottom. This permits measurement of the bulk shrinkage of a cementitious mix 54. Temperature of the mix may be measured with a thermocouple 55.

Figure 4:
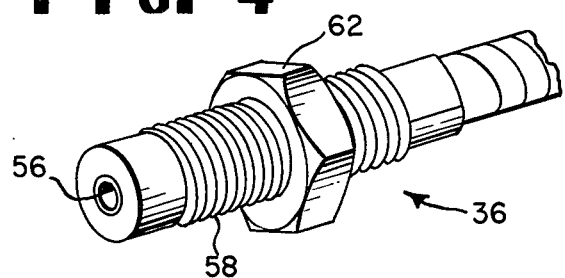
FIG. 4 is an enlarged, perspective view of the proximity transducer shown in FIGS. 1 and 2.
Figure 4:
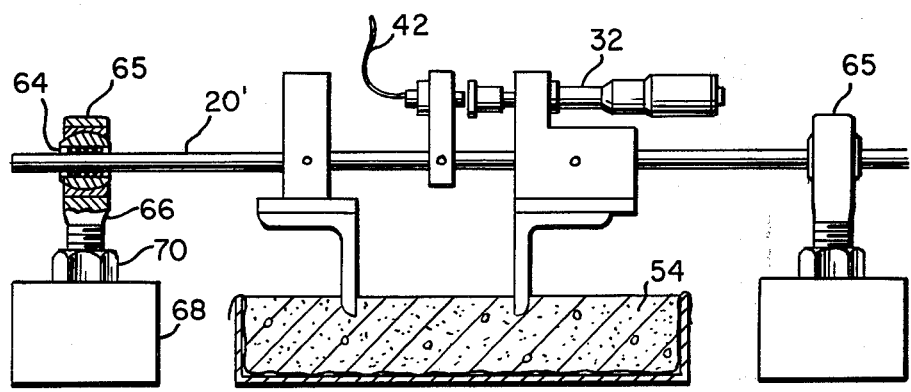

Transducer 36 functions as a noncontacting, electronic micrometer for measuring variations in the gap between target disc 38 and a probe tip 56 (FIG. 4) in the transducer. The probe and other essential parts of the transducer 36 are mounted in a metallic casing having a threaded length 58 that is screwed through an aperture in an arm 60. Arm 60 is fixed with respect to shaft 20. When properly positioned, the transducer is locked in place with a jam nut 62. Proximeter 40 transmits electrical energy from source 46 to the probe and adjusts the inductive signal returned from the probe to provide a voltage that is proportional to any distance change detected by the probe. That voltage response is linear through a range of variations in the initially set distance between probe tip 56 and target disc 38.

The modified shrinkage gauge shown in FIG. 5 has a longer shaft 20', the ends of which are received by ball bushings 64 in the balls of ball-and-socket joints 65 at the upper ends of rod ends 66. Rod ends 66 are threaded into apertures in blocks 68. When the rod ends are properly positioned, with blades 16 at the desired depth in mix 54, they can be locked in place by jam nuts 70.

In an embodiment used to measure and record the cure shrinkage of various cementitious materials, transducer 36 is a Bently Nevada proximity probe, No. 190-00-00-07-36-02. Proximeter 40 is also a Bently Nevada instrument, No. 3115-2800-190. Strip chart recorder 50 is a Speedomax M, Mk.III, Leeds & Northrup. Supports 66 are Alinabal rod ends, Part WM-10-B2. Bushings 26, 64 are Thomson ball bushings, No. A-61014.

Tests are normally made at room temperature but, with calibration of recorder 50, can be conducted in other environments. The material to be tested is mixed, placed in mold box 52, and floated like concrete. A wooden box having a length of twenty (20) inches, a width of ten (10) inches and a depth of two (2) inches is used. Floating is accomplished on a vibrating table (SOILTEST, Model CT-164). To insure unrestrained shrinkage, the inner surface of the mold box is coated with grease and a layer of polyethylene film 72 is applied. The shrinkage gauge is prepared by attaching two blade feet and fixing the distance between the blades 16 at ten (10) inches by inserting locking pin 28. In addition, the strip chart recorder 50 is calibrated, using micrometer head 32, into the linear range of transducer 36.

When the mix 54 is ready, the gauge is inserted, in the center of mold box 52, and blades 16 penetrate through the mix to the bottom of the box. Strip chart recorder 50 is set at the desired set point and locking pin 28 is removed. Because of the low friction between bushing 26 and shaft 20, blades 16 are free to move with mix 54 as it cures. In this manner, very small changes in the distance between probe tip 56 and disc 38 can be monitored continuously. To measure the temperature of mix 54 during the exothermic curing and subsequent cooling of polymeric concrete, the thermocouple 55 is inserted in mix 54.

The readings on strip recorder 50 will show the change in length, i.e., expansion and/or shrinkage of mix 54, between the blades 16. If this distance exceeds the range of strip recorder 50 or the linear range of transducer 36, micrometer head 32 can be adjusted to return the recorder pen position to the usable linear range.

At the completion of the test, mounting plates 14 are disengaged from base plates 10, 12 and the expendable blade feet are left in the cured test mix. The gauge is removed and new blade feet are attached in preparation for the next test.

If the mix 54 is deep and stiff enough, the gauge can be inserted until mounting plates 14 touch the surface of the mix. The gauge will then "float" on the mix 54.

When it is desired to control the depth to which blades 16 will be inserted, the shaft 20' and supports shown in FIG. 5 are used. An empty mold box 52 is placed under the gauge and the depth of the feet is set at the desired level by adjusting rod ends 66. Shim blocks can be placed under height blocks 68 to make major changes in depth. Once the depth is set, the steps described above are followed.

As noted, the method of testing disclosed herein includes the preliminary steps of coating the mold box 52 with grease and lining it with a layer 72 of thin, plastic film. Thus, cementitious materials are not restrained by their tendency to bond with surrounding surfaces. If the mold boxes are filled to the same depth, unrestrained shrinkage information obtained in tests of different cementitious materials in the same environment can be compared directly. The test data can be correlated with actual shrinkage in well bonded repairs and used to predict the likelihood of a crack-free installation. Information such as this is useful, for example, in planning the materials and formulations to be used in making repairs or applying surfaces at different temperatures.

The gauge and method are particularly useful in tests of rapidly curing, cementitious materials that include monomeric or resinous bonding agents. During the cure of materials including monomeric bonding agents, monomer is converted to polymer with an evolution of heat. The continuous record made on strip chart recorder 50 during a test, along with periodic readings of temperature, shows a measurable expansion during exothermic heating as well as a direct relationship between the peak exotherm and both the extent and timing of cure shrinkage. Furthermore, tests of the same materials at different temperatures allow evaluations of the mechanisms involved in cure shrinkage, namely, polymerization shrinkage and thermal contraction. For example, pilot tests have shown that installation at ambient temperatures of 30° F. vice 75° F. can decrease the unrestrained cure shrinkage of the same polymer concrete by about two-thirds.

What is claimed as new and desired to be secured by Letters Patent is:

1. A shrinkage gauge comprising:
   an elongated bridge member;
   a pair of dependent blades, one fixed, the other slidable with respect to said bridge member;
   means releasably locking said slidable blade with respect to the bridge member with the blades a set distance apart;
   a proximity transducer fixedly attached to the bridge member; and
   a target attached to said slidable blade, said transducer having a probe tip spaced from and aligned with said target, said blades being in substantial parallelism and adapted for insertion in poured cementitious materials.

2. The gauge of claim 1 further comprising means mounting said target for adjustments toward and away from the probe tip.

3. The shrinkage gauge of claim 1 further comprising a pair of blocks, one fixed, the other slidable with respect to said bridge member, and removable fasteners attaching the blades thereto.

4. The shrinkage gauge of claim 3 further comprising an arm fixed to and extending outwardly from said bridge member between said blocks, said transducer being attached to said arm.

5. The shrinkage gauge of claim 4 further comprising a pair of supports for the ends of said bridge member, each support including means for adjusting the depth of insertion of the blades.

6. A member comprising the steps of:
   locating a pair of blades in substantial parallelism and a set distance apart, with their ends sunk in poured cementitious materials;
   allowing the materials to cure; and
   measuring and recording continuously relative movement between the blades as an indication of expansion and/or shrinkage during curing.

7. The method of claim 6 further comprising the preliminary steps of lining a mold box with a plastic film and pouring the materials into the lined box.

8. The method of claim 7 wherein the materials include monomeric bonding agents.

9. The method of claim 6 further comprising the steps of measuring and recording the temperature of the materials during the cure cycle.

* * * * *